United States Patent [19]

Michaely

[11] 4,118,400

[45] Oct. 3, 1978

[54] PROCESS FOR PREPARING 2,3-DIHYDRO-7-BENZOFURANOLS AND BENZODIOXOLE INTERMEDIATE THEREFOR

[75] Inventor: William James Michaely, Princeton Junction, N.J.

[73] Assignee: FMC Corporation, Philadephia, Pa.

[21] Appl. No.: 835,630

[22] Filed: Sep. 22, 1977

[51] Int. Cl.² .................. C07D 317/46; C07D 307/86
[52] U.S. Cl. .............................. 260/340.5; 260/346.22
[58] Field of Search ........................ 260/346.22, 340.5

[56] References Cited

U.S. PATENT DOCUMENTS

| | | | |
|---|---|---|---|
| 2,169,984 | 8/1939 | Weissenborn | 260/340.5 |
| 3,320,286 | 5/1967 | Franko-Filipasic | 260/346.73 |
| 3,356,690 | 12/1967 | Orwall | 260/346.73 |
| 3,419,579 | 12/1968 | Towns | 260/346.73 |
| 3,474,170 | 10/1969 | Scharpf | 424/285 |
| 3,474,171 | 10/1969 | Scharpf | 424/285 |
| 3,682,973 | 8/1972 | Eriksoo et al. | 260/340.5 |
| 3,736,338 | 5/1973 | Gates et al. | 260/340.5 |
| 3,816,473 | 6/1974 | Serban et al. | 260/346.73 |
| 3,822,295 | 7/1974 | Serban et al. | 260/346.73 |
| 3,876,667 | 4/1975 | Serban et al. | 260/346.73 |

*Primary Examiner*—Henry R. Jiles
*Attorney, Agent, or Firm*—Robert L. Andersen; H. Robinson Ertelt

[57] ABSTRACT

A 2,3-dihydro-7-benzofuranol having the formula

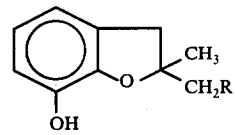

is prepared by thermally rearranging a 1,3-benzodioxole of the formula

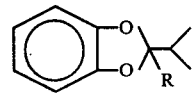

4 Claims, No Drawings

PROCESS FOR PREPARING 2,3-DIHYDRO-7-BENZOFURANOLS AND BENZODIOXOLE INTERMEDIATE THEREFOR

BACKGROUND OF THE INVENTION

1. Field of Invention

The present invention relates to a process for preparing a 2,3-dihydro-7-benzofuranol from a 1,3-benzodioxole and to a novel 1,3-benzodioxole utilized in the process. More particularly the invention relates to thermal rearrangement of 2-substituted 1,3-benzodioxoles in the presence of an acid or transition element catalyst to form 2-substituted 2,3-dihydro-7-benzofuranol.

2. Description of the Prior Art 2,3-Dihydro-7-benzofuranols which are substituted at the 2 position are known intermediates for the preparation of benzofuranyl carbamate insecticides such as those set forth in U.S. Pat. Nos. 3,470,299, 3,474,170 and 3,474,171. Several routes are known for preparing these 2,3-dihydro-7-benzofuranols. Some of these are set forth in the foregoing patents and in Franko-Filipasic, U.S. Pat. No. 3,320,286, which discloses a process now in commercial use. In this process for preparing 2,3-dihydro-2,2-dimethyl-7-benzofuranol, o-nitrophenol is first reacted with methallyl halide. The resulting o-methallyloxynitrobenzene is thermally rearranged then cyclized to 2,3-dihydro-2,2-dimethyl-7-nitrobenzofuran. The latter is then successively reduced, diazotized, and hydrolyzed.

The object of the present invention is to provide a more direct route to 2,3-dihydro-7-benzofuranols substituted at the 2 position. It has now been found that these compounds are readily prepared by thermally rearranging a corresponding 2-substituted-1,3-benzodioxole.

SUMMARY OF THE INVENTION

The present invention is a process for preparing a 2,3-dihydro-2,2-substituted-7-benzofuranol, I,

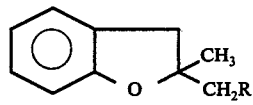

by thermally rearranging a 2-isopropyl-1,3-benzodioxole, II,

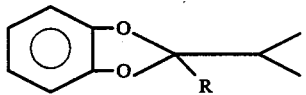

in the presence of a suitable catalyst or catalyst mixture.

DETAILED DESCRIPTION OF THE INVENTION

In the preferred embodiment 2-isopropyl-1,3-benzodioxole is prepared by reacting catechol with isobutyraldehyde, III, in the presence of a condensation catalyst in accordance with the equation:

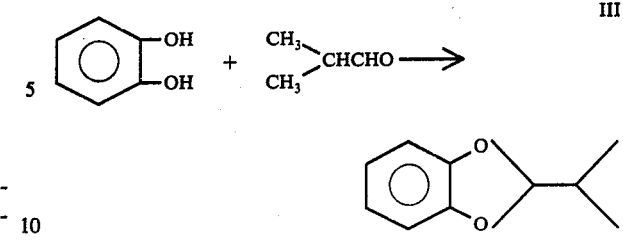

The reaction is conducted by heating catechol and the isobutyraldehyde, preferably dissolved in a suitable solvent, for example, benzene, at a temperature of 30° C. up to the boiling point of the solvent, about 80° C. for benzene. Catalysts for the reaction include a catalytic amount of an acid acetalization catalyst such as sulfuric acid, phosphoric acid, polyphosphoric acid, hydrochloric acid, aliphatic or aromatic sulfonic acid, trifluoroacetic acid, and the like. Example I demonstrates the preferred compound and its preparation.

EXAMPLE I

Catechol (22 g, 0.2 mole) and isobutyraldehyde (16 g, 0.24 mole) were dissolved in benzene (600 ml). A catalytic amount (5 drops) of sulfuric acid was added to the mixture. The mixture was heated under reflux and the water formed in the reaction was removed by use of a Dean-Stark trap. The reaction mixture was washed twice with aqueous sodium carbonate solution and dried. 2-Isopropyl-1,3-benzodioxole (11 g, 0.067 mole) was obtained by vacuum distillation. The 2-isopropyl-1,3-benzodioxole thus obtained boiled at 29–31° C. at 0.25 mm Hg. The nmr spectrum was consistent with the assigned structure.

In the preferred embodiment the 2-isopropyl-1,3-benzodioxole is thermally rearranged to form 2,3-dihydro-2,2-dimethyl-7-benzofuranol, IV, in accordance with the equation

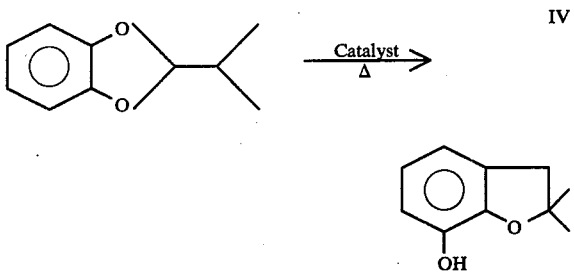

by heating the 2-isopropyl-1,3-benzodioxole in the presence of an acid catalyst at a temperature above about 135° C., suitably to a temperature in the range of 135° to 300° C. Suitable acid catalysts include a wide range of acid clays or Lewis acids such as $MgCl_2$ or $ZnCl_2$. These may be used alone or in combination with Group VIII transition metal catalysts such as nickel, palladium or platinum, preferably in a finely divided form on a suitable carrier, for example palladium on carbon. The preferred catalyst is a mixture of Lewis acid and finely divided transition metal.

The acid clays useful in the present invention are preferably those which are acid activated and have an acid value of 1.0–16 mg KOH per gram of clay, preferably 1.7 to 8, a surface area of about 200 to 350 sq M./gm and a particle size such that at least 90% and preferably 95 to 100% will pass through a 100 mesh Tyler Standard Sieve. Acid clays of the montmorillonite group or of the kaolinite group, as classified in Lange's Handbook of Chemistry, 9th ed. (1957) pp 204–207 may be employed in the present invention. Typical clays of the montmorillonite group are those sold under the brand name "SUPER FILTROL" by FILTROL Corporation, 5959 West Century Blvd., Los Angeles, Calif. 90045.

The presence of a solvent is not required, but may be employed if desired. Suitable solvents include benzene, toluene, o-dichlorobenzene, monochlorobenzene and other similar solvents which may be selected without departing from the spirit and scope of the invention.

Reaction time will vary considerably with the temperature, catalyst and solvent employed. In general, a reaction (heating) time of about 0.5 hours up to about 25 hours is suitably employed. The following example demonstrates the preparation of the 2,3-dihydro-7-benzofuranol using a clay catalyst.

EXAMPLE II

2-Isopropyl-1,3-benzodioxole (2.0 g) was heated to 235° C. in the presence of 75 mg of an acidic clay of the montmorillonite group [tradename SUPER FILTROL] for four hours. Gas chromatographic analysis indicated that the resulting reaction mixture contained 13.48% 2,3-dihydro-2,2-dimethyl-7-benzofuranol. The reaction product was isolated by base extraction and acidification of the basic extract to separate the extracted 2,3-dihydro-2,2-dimethyl-7-benzofuranol. The identity of the product thus obtained was confirmed by comparing its ir spectrum, thin layer chromatograms on silica gel, and glc retention time, with the same data obtained for a known sample of 2,3-dihydro-2,2-dimethyl-7-benzofuranol.

EXAMPLE III

This example exemplifies the use of a combined catalyst system. A mixture of 10g 2-isopropyl-1,3-benzodioxole (IPBD) 20g dichlorobenzene, 0.5g MgCl$_2$ and 0.2g Pd/C, was heated to reflux (183°–4° C.) for 6.9 hours. Periodically 1 ml samples were removed, chilled to room temperature and filtered. The filtrates were analyzed by gas chromatography against standards for product, and product yield was determined for each sample in accordance with the formula:

yield (mole %) = B/(A$_1$ − A$_2$) × 100 where B is moles of product, A$_1$ is moles of IPBD before reaction, and A$_2$ is moles of IPBD remaining. Yields are reported in Table 1. Conversion was 1.0 to 1.2 mole percent for the values reported.

Table 1

| Sample TIME (HRS) | Yield (mole %) |
|---|---|
| 1.1 | 64 |
| 2.1 | 62 |
| 3.1 | 63 |
| 3.9 | 62 |
| 4.9 | 52 |
| 6.9 | 54 |

It is also contemplated that other 2-substituted-7-benzofuranols may be prepared by reacting catechol with a lower alkyl isopropyl-ketone, as in Example I, in accordance with the general equation,

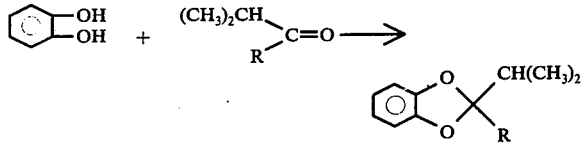

wherein R is lower alkyl, preferably methyl or ethyl, and then thermally rearranging as in Example II, in accordance with the general equation

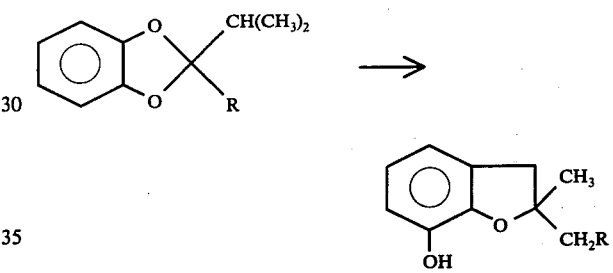

Thus, R is methyl in the production of 2,3-dihydro-2-ethyl-2-methyl-7-benzofuranol and is ethyl for the production of 2,3-dihydro-2-methyl-2-propyl-7-benzofuranol.

I claim:

1. A process for preparing 2,3-dihydro-2,2-dimethyl-7-benzofuranol which comprises thermally rearranging 2-isopropyl-1,3-benzodioxole at a temperature above about 135° C. in the presence of a catalytic amount of a catalyst selected from the group consisting of (1) an acid clay having an acid value of 1 mg to 16 mg potassium hydroxide per gram of clay and (2) a Lewis acid.

2. The process of claim 1 wherein said catalyst is employed in admixture with a Group VIII transition metal catalyst.

3. The process of claim 1 wherein said 2-isopropyl-1,3-benzodioxole is rearranged by heating at a temperature of 135° to 300° C.

4. The compound 2-isopropyl-1,3-benzodioxole.

* * * * *

UNITED STATES PATENT AND TRADEMARK OFFICE
CERTIFICATE OF CORRECTION

PATENT NO. : 4,118,400
DATED : October 3, 1978
INVENTOR(S) : William James Michaely It is certified that error appears in the above—identified patent and that said Letters Patent are hereby corrected as shown below:

Column 1, line 45, the structure (I) should read as follows:

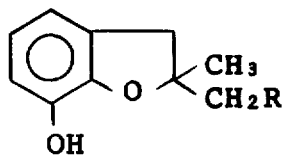   I

Signed and Sealed this

Twentieth Day of March 1979

[SEAL]

Attest:

RUTH C. MASON
Attesting Officer

DONALD W. BANNER
Commissioner of Patents and Trademarks